United States Patent [19]
Greenspan et al.

[11] Patent Number: 6,037,139
[45] Date of Patent: Mar. 14, 2000

[54] SYSTEM FOR ASSAYING MODULATORS OF PROCOLLAGEN MATURATION

[75] Inventors: Daniel S. Greenspan, Madison, Wis.; Seungbok Lee, Nashville, Tenn.

[73] Assignee: Wisconsin Alumni Research Foundation, Madison, Wis.

[21] Appl. No.: 08/868,420

[22] Filed: Jun. 3, 1997

[51] Int. Cl.⁷ ......................... C12Q 1/37; C07K 14/495; C12N 9/50

[52] U.S. Cl. ........................... 435/23; 435/219; 435/325; 530/350; 530/356

[58] Field of Search ........................... 435/23, 325, 219; 530/350, 256

[56] References Cited

U.S. PATENT DOCUMENTS

| 4,579,821 | 4/1986 | Palmiter et al. | 435/172.3 |
| 5,807,981 | 9/1998 | Brenner | 530/327 |

FOREIGN PATENT DOCUMENTS

| WO 94/22487 | 10/1994 | WIPO. |
| WO 97/05865 | 2/1997 | WIPO. |
| WO 97/06242 | 2/1997 | WIPO. |
| WO 97/45528 | 12/1997 | WIPO. |

OTHER PUBLICATIONS

Abe et al. An assay for transforming growth factor–beta using cells transfected with a plasminogen activator inhibitor–1 promoter–luciferase construct. Anal. Biochem., (Feb. 1, 1994) 216 (2) 276–84.

Feres–Filho et al. Pre–and post–translational regulation of lysyl oxidase by transforming growth factor–beta 1 in osteoblastic MC3T3–E1 cells. J Biol Chem Dec. 22, 1995;270(51):30797–803.

Martin et al. "Osteoblasts: Differentitation and Function", In, Physiology and Pharmacology of Bone vol. 107, eds. Mundy et al., Springer–Verlag, 1993.

Shah et al. Neutralisation of TGF–beta 1 and TGF–beta 2 or exogenous addition of TGF–beta 3 to cutaneous rat wounds reduces scarring. Journal of Cell Science, (Mar. 1995) 108 (Pt 3) 985–1002.

Centrella et al. Multiple regulatory effects by transforming growth factor–beta on type I collagen levels in osteoblast–enriched cultures from fetal rat bone. Endocrinology, (Dec. 1992) 131 (6) 2863–72,Feb. 1992.

Chan et al. Regulation of procollagen synthesis and processing during ascorbate–induced extracellular matrix accumulation in vitro. Biochem. J., (Jul. 1, 1990) 269 (1) 175–81.

Keski–Oja et al. Regulation of mRNAs for type–1 plasminogen activator inhibitor, fibronectin, and type I procollagen by transforming growth factor–beta. Divergent responses in lung fibroblasts and carcinoma cells. J. Biol. Chem., (Mar. 5 1988) 263 (7) 3.

Hojima et al., "Cadmium Ions Inhibit Procollagen C–Proteinase and Cupric Ions Inhibit Procollagen N–Proteinase," *Matrix Biology* 14:113–120 (1994).

Lee et al., "Transforming Growth Factor–β Regulation of Bone Morphogenetic Protein–1/Procollagen C–proteinase and Related Proteins in Fibrogenic Cells and Keratinocytes," *The Journal of Biological Chemistry* 272:19059–19066 (1997).

Bond, Judith S. and Beynon, Robert J., "The Astacin Family of Metalloendopeptidases", *Protein Science* 4: 1247–1261 (1995).

Colige et al., "cDNA Cloning and Expression of Bovine Procollagen I N–proteinase: A New Member of the Superfamily of zinc–metalloproteinases with Binding Sites for Cells and other Matrix Components", *PNAS USA* 94:2374–2379 (1997).

Greenspan, D.S., "Mus Musculus Mammalian Tolloid–Like Protein mRNA", Genebank Accession No. U34042. Submitted Aug. 15, 1995.

Johnson, George, "The Chicken with a Duck's Feet: It's All in the Biochemical Signal", The New York Times *Science* (May 21, 1996.

Kessler et al., "Bone Morphogenetic Protein–1: The Type I Procollagen C–Proteinase", *Science* 271: 360–362 (1996).

Nguyen et al., "Characterization of tolloid–related–1: A BMP–1–like Product that is Required During Larval and Pupal Stages of Drosophila Development", *Developmental Biology* 166: 569–586 (1994).

Takahara et al., "Type I Procollagen COOH–terminal Proteinase Enhancer Protein: Identification, primary Structure, and Chromosomal Localization of the Cognate Human Gene (PCOLCE)", *J. Biol. Chem.* 269(42): 26280–26285 (1994).

Takahara et al., "Bone Morphogenetic Protein–1 and a Mammalian Tolloid Homolgue (mTld) Are Encoded by Alternatively Spliced Transcripts Which Are Differently Expressed in Some Tissues" *J. Biol. Chem.* 269 (51): 32572–32578 (1994).

Takahara et al., "Characterization of a Novel Gene Product (Mammalian Tolloid–Like) with High Sequence Similarity to Mammalian Tolloid/Bone Morphogenetic Protein–1", *Genomics* 34:157–165 (1996).

Takahara et al., "Structural Organization and Genetic Localization of the Human Bone Morphogenetic Protein 1/Mammalian Tolloid Gene", *Genomics* 29:9–15 (1995).

Wozney et al., "Novel Regulators of Bone Formation: Molecular Clones and Activities", *Science* 242: 1528–1534 (1988).

ATCC Cell Lines & Hybridomas. Paperback, 632 Pages, Edition No. 08, American Type Culture Collection, ISBN: 0930009541, Editor: Hay, Robert/Chen, T. R. / Macy, Marvin / McClintock, Patrick / Reid, Yvonne / Caputo, Jane. p. 43, 1994.

Alberts et al., Molecular Biology of the Cell, Jan. 1994, Garland Publishing, Inc., New York, NY, p. (s) 111, Jan. 1994.

*Primary Examiner*—Elizabeth Kemmerer
*Assistant Examiner*—David S. Romeo
*Attorney, Agent, or Firm*—Quarles & Brady LLP

[57] ABSTRACT

Potential modulators of a procollagen-cleaving enzyme are assessed by determining the ability of the enzyme to cleave procollagen in the presence and absence of a potential modulator in the culture medium of cells induced to secrete a procollagen-cleaving enzyme.

8 Claims, No Drawings

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 17 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

```
Cys Pro His Gln Leu Lys Phe Arg Val Gln Lys Arg Asn Arg Thr Pro
1               5                   10                  15
Gln
```

(2) INFORMATION FOR SEQ ID NO:2:

(i) SEQUENCE CHARACTERISTICS:
      (A) LENGTH: 17 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

```
Cys Leu Arg Tyr Thr Ser Thr Lys Phe Gln Asp Thr Leu His Ser Arg
1               5                   10                  15
Lys
```

(2) INFORMATION FOR SEQ ID NO:3:

(i) SEQUENCE CHARACTERISTICS:
      (A) LENGTH: 17 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:3:

```
Asp Leu Ala Glu Glu Asp Asp Ser Glu Pro Leu Asn Tyr Lys Asp Pro
1               5                   10                  15
Cys
```

SYSTEM FOR ASSAYING MODULATORS OF PROCOLLAGEN MATURATION

CROSS-REFERENCE TO RELATED APPLICATIONS

Not applicable.

STATEMENT REGARDING FEDERALLY SPONSORED RESEARCH OR DEVELOPMENT

Not Applicable.

BACKGROUND OF THE INVENTION

The molecular basis of extracellular matrix deposition has been a subject of great interest in recent years. As the molecular components have become known, attention has shifted toward developing pharmaceutical and therapeutic interventions for controlling particular steps in the relevant deposition processes. One critical step is the production of mature triple helical fibrillar collagen, Types I–III. These collagen molecules are synthesized as procollagen precursors that contain amino-terminal (N-) and carboxyl-terminal (C-) propeptides that are cleaved extracellularly to yield the mature triple helical collagen monomers that can associate into fibrils that can themselves be deposited in a matrix (for a review, see Ref. 5). The N- and C-terminal cleavages are accomplished by distinct enzymatic activities, that have been denoted procollagen C-proteinase (PCP) (8–10) and procollagen N-proteinase (PNP) (47).

It would be desirable, for example in the field of wound healing, to modulate the kinetics of collagen deposition. One promising mechanism for doing so is to alter collagen maturation by modulating the activities of PCP and PNP. The efforts of pharmaceutical developers have been hampered by the lack of an effective system for assaying the modulating effects of putative agents that affect PCP and PNP activities. Before therapeutic development can proceed in an in vivo system, an in vitro system is needed that can determine both whether an agent is effective for modulating the maturation of procollagen to collagen and whether the agent is itself toxic to fibrogenic cells.

Recently, the bone morphogenetic protein-1 (BMP-1) was shown to be identical to procollagen C-proteinase (PCP)(6, 7), the activity that cleaves the C-propeptides of procollagen types I–III (8–10). The mammalian BMP1 gene that encodes BMP-1 also produces an alternatively spliced mRNA that encodes mammalian tolloid (mTld), a longer protein that has a domain structure identical to that of Drosophila Tld (4). mTld also has PCP activity (7). The necessary action of BMP-1 and mTld in processing of matrix components (6,7,12) and lysyl oxidase (11) suggests that these proteins play key roles in controlling the deposition of matrix in developmental and homeostatic processes. Previously, however, mechanisms for regulating functional expression of these key proteins have not been explored.

BMP-1 copurifies from osteogenic bone extracts with transforming growth factor-$\beta$ (TGF-$\beta$)-like proteins BMP-2 through -7 (1). Thus, it was suggested that BMP-1, by structure an astacin-like protease, may function in morphogenesis by activating TGF-$\beta$-like molecules (1). Consistent with this possibility, BMP-1 has a domain structure similar to, but shorter than that of tolloid (Tld), a Drosophila protein that appears to act in patterning of embryos by potentiating the activity of decapentaplegic, a TGF-$\beta$ family member (2,3).

PCP activity of BMP-1 is stimulated ~10-fold by the procollagen C-proteinase enhancer (PCPE), a glycoprotein that binds the type I procollagen C-propeptide (10). However, possible involvement of PCPE in other biological activities of BMP-1 and mtld has not been examined.

TGF-$\beta$1, prototype of the TGF-$\beta$ superfamily, induces net increases in deposition of insoluble matrix by cells. This is accomplished by effecting decreased production of proteases that degrade matrix, and increased production of i) inhibitors for such proteases, ii) structural matrix components such as procollagen types I–III (13), and iii) lysyl oxidase (14). Expression of the genes for the three polypeptide chains of laminin 5 is also upregulated by TGF-$\beta$ in keratinocytes (15).

BRIEF SUMMARY OF THE INVENTION

In a cell culture system for assaying the effects of a modulator of procollagen maturation, fibrogenic cells secrete into the culture medium a biologically active form of a procollagen-cleaving enzyme (or an enzymatic activity) at a level sufficiently high that procollagen maturation can be assayed in the medium or in the extracellular matrix associated with the cell layer in the presence or absence of a putative modulator of collagen maturation. The profile of procollagen cleavage products can be monitored by immunoassays such as Western blots. The inventors are unaware of any cultured fibrogenic cell type that secretes a sufficiently high level of such an active enzyme or enzymatic activity to facilitate use in an assay of the type described.

A suitable cell culture system can be created by culturing suitable fibrogenic cells in a culture medium containing an amount of an inducing molecule that induces increased secretion of a procollagen-cleaving enzyme (or an enzymatic activity) into the culture medium to a level sufficiently high that an assay of the type described can be performed.

It is an object of the present invention to provide a convenient cellular system for evaluating collagen maturation in the presence or absence of a putative modulator of procollagen maturation.

It is an advantage of the present invention that the putative modulator can be provided in the cell culture medium at the same time as the inducing molecule is provided.

Other objects, advantages and features of the present invention will become apparent upon consideration of the following detailed description of the invention.

BRIEF DESCRIPTION OF THE SEVERAL VIEWS OF THE DRAWINGS

Not applicable.

DETAILED DESCRIPTION OF THE INVENTION

The inventors here disclose that the procollagen-cleaving enzymes of fibrogenic cells are themselves upregulated at the mRNA and protein levels by an inducing molecule. The inventors have observed that treatment of fibrogenic cells with TGF-$\beta$ increases BMP-1, mTld, and PNP mRNA and protein levels. Further, the induced enzymes are presented in an active form in suitable fibrogenic cells. It is known that PCP/BMP-1 is processed from a proenzyme form. PNP may also be similarly processed.

This new understanding is advantageously applied to create a cellular system for assaying the effects of a putative modulator of procollagen maturation. In the system, fibrogenic cells are grown in a culture medium that sustains cell growth and comprises an inducing molecule, preferably a member of the transforming growth factor superfamily, that can increase secretion of a procollagen-cleaving enzyme (or an enzymatic activity) from the fibrogenic cells into the culture medium to a level sufficiently high that an assay of the type described can be performed.

Extracellular procollagen maturation is effected by secreted molecules having procollagen-cleaving activity. A procollagen-cleaving molecule cleaves either an N-terminal peptide or a C-terminal peptide from procollagen to produce mature collagen monomers. A procollagen-cleaving molecule that effects procollagen maturation can be a naturally occurring protein or peptide, such as BMP-1 or mTld, both of which are known to have procollagen C-proteinase enzymatic activity. A PNP protein encoding the procollagen N-proteinase having activity against procollagen Types I and II has been identified (47). It is thought that a separate PNP protein acts against procollagen Type III. The procollagen-cleaving molecule can also be an identified enzymatic activity not yet associated with a particular protein. Furthermore, the procollagen-cleaving enzyme can be a synthetic molecule that has the indicated N- or C-terminal cleavage activity, whether the molecule is created by in vivo or in vitro recombination or by methods of genetic engineering known to those skilled in the art, or by another method. It is only important that the cleaving molecule cleave procollagen at a detectable level that can be compared against a test system that further comprises a putative modulator of such cleavage. Moreover, it is sufficient that cleavage occur at only the N- or the C-terminus of the procollagen protein, since procollagen maturation can be modulated by a change in the extent of cleavage at either end of the protein. It is acceptable, but not essential, that cleavage occur at both ends of the procollagen protein. A suitable inducing molecule induces a procollagen-cleaving enzyme, but is not toxic to the cells, as determined using a standard typically used in the pharmaceutical industry for balancing activity against toxicity. It may be that permissible toxicity in culture may be higher than would be suitable in vivo. However, those skilled in the art of pharmaceutical development and testing are able to assess toxicity. It would be suitable to assess toxicity to the treated cells in culture, using, for example, a trypan blue exclusion assay.

It is preferred that the inducing molecule be a member of the TGF-β superfamily. Because of the close similarity of these members, it is believed that other members of the family now known or in the future discovered would be suitable. It is possible that other inducing agents will function in an equivalent manner. Since TGF-β1 is the prototype family member and has been shown to function in the assay, it is considered a preferred inducing agent. Other suitable members of the superfamily include TGF-β2. A suitable concentration of TGF-β1 in the medium is 0.01 to 25 ng/ml, preferably 0.5 to 10 ng/ml, and more preferably 1 to 5 ng/ml. Maximal production of BMP-1 and mTld is observed at about 2 ng/ml in MG-63 osteosarcoma cells. Addition of ascorbate to the culture medium with TGF-β also seems to further increase the levels of activated forms of procollagen-cleaving enzymes. Ascorbate is also a necessary cofactor for enzymic hydroxylation of collagen prolyl residues, leading to a more stable procollagen triple helix and, thus, a more suitable endogenous substrate (35).

The amount of the inducing molecule needed can vary in accordance with the treated cell type. One skilled in the art can readily perform simple and routine experiments to optimize the concentration of the inducing molecule in the medium.

The production of procollagen-cleaving enzymes is also time-dependent after induction. Culture for between 6 and 12 hours in the presence of TGF-β1 inducing agent is required to accumulate sufficient BMP-1 or mTld. This delay suggests that the TGF-β1 is not the direct inducer, but rather that activation of a procollagen-cleaving enzyme results from one or more intermediate induction steps. This hypothesis is strengthened by the observation that activation is prevented if protein synthesis cannot occur after treatment with TGF-β1.

A putative modulating agent can be added into the culture medium over a range of concentrations and evaluated for its effect on one or more procollagen cleaving enzymes secreted into the medium from the test cells. A suitable range of modulating agent concentrations that have a modulating effect can be in the range of nM to μM, although particularly effective or ineffective modulators can require more or less. An agent is said to have a modulating effect if under the tested conditions it increases, or preferably decreases, the procollagen cleavage relative to the cleavage levels observed in untreated cells.

A modulating agent can be any such agent having the desired effect, and one skilled in the art will be guided in selecting a modulating agent on the basis of known modulators (especially inhibitors) of protease activity. Suitable molecules can include small organic, aromatic compounds. Antibodies directed against active sites on the target enzymes may also be effective modulators.

A modulating effect on procollagen maturation can be assayed by probing for one or more processing intermediates or products that comprise the cleavage profile of procollagen. The procollagen target can be secreted from the tested cells or can be exogenously added to the culture medium. The following processing intermediates and products are formed by cleavage of Type I procollagen [proα1(I)] during maturation:

pNα1(I): contains N- but not C-propeptide pCα1(I): contains C- but not N-propeptide α1(I): fully processed helical Type I collagen protein monomer These intermediates and products can be detected by antibodies raised against particular amino acid sequences, as is described in more detail in the Examples. Western blotting using sequence-specific antibodies as probes is an appropriate method for assessing cleavage profiles. In a typical assay, cells are exposed to the inducing agent (with or without the putative modulator) for 48 hours if protein will be analyzed. Production of such antibodies is routine to those skilled in the art. One skilled in the art will appreciate that it may be necessary to adjust the concentration range of the putative modulating agent before concluding that an agent has, or does not have, a desired effect. The invention is disclosed using type I collagen as an exemplary embodiment, however the processing of type II and type III collagen could be evaluated in the assay with equivalent effect.

The procollagen-cleaving enzyme is preferably secreted from a suitable cellular system in an active form, although it may be possible to convert an inactive secreted proenzyme to an active form before performing the modulation assay described herein. Because fibrogenic cells secrete an active form of the procollagen-cleaving enzymes, such cells are considered to be a preferred cell type for use in the system. More preferred cell types also comprise the procollagen C-proteinase enhancer (PCPE), a glycoprotein that stimulates PCP activity. Although neither PCPE production nor PCPE activity need be elevated in the present invention, the presence of PCPE in the cells increases the overall procollagen-cleaving activity of the cells.

It is also desirable for the cells to produce suitable levels of unprocessed procollagen which can be the substrate for the procollagen-cleaving enzyme. The procollagen can alternatively be exogenously provided. The procollagen and its cleavage products should be detectable, for example, by Western blot under standard conditions. It is also contemplated that the assay described herein can be performed on metabolically labelled procollagen.

Suitable cell types for use in the system are human osteosarcoma cells [especially MG-63 (available from American Type Culture Collection, Rockville, Md., Accession Number CRL-1427)] or murine osteoblastic cells [especially MC3T3-E1 (which is widely available to those skilled in the art)] or normal human dermal fibroblasts. In MG-63 osteosarcoma cells, which display a TGF-β receptor, exposure to TGF-β1 elevated levels of BMP-1 mRNA about 7-fold, and elevated levels of mTld mRNA to a lesser extent, relative to the levels of each in MG-63 cells not treated with TGF-β1. BMP-1 mRNA levels were elevated in a dose- and time-dependent manner, and could be inhibited by cycloheximide. Secreted BMP-1 and mTld, induced by TGF-β1 in MG-63 and other fibrogenic cell cultures, were predominantly in forms in which proregions had been removed to yield activated enzyme. TGF-β1 treatment also induced procollagen N-proteinase mRNA in MG-63 cell cultures, and likely also increases protein levels as well.

Less preferred are cells that secrete inactive proenzymes, such as non-fibrogenic keratinocytes. Keratinocytes lacked detectable PCPE under any culture conditions and were induced by TGF-β1 to secrete BMP-1 and mtld predominantly as unprocessed proenzymes.

The present invention will be further understood upon consideration of the following examples which are intended to be exemplary and not limiting on the scope of the invention.

EXAMPLES

Cell Culture

MG-63 human osteosarcoma cells, MC3T3-E1 murine osteoblastic cells, and AH1F human neonatal foreskin fibroblasts cells were maintained in Dulbecco's modified Eagle's medium with 10% heat-inactivated (30 min, 55° C.) fetal calf serum (FCS). MC3T3-E1 cells were supplemented with 1% nonessential amino acids. When RNA was prepared from MG-63 cells, media contained 0.1% heat-inactivated FCS. When samples for immunoblots were prepared from MG-63, MC3T3, or AH1F cultures, media was serum free, unless otherwise indicated. Primary human keratinocytes were maintained in 0.15 mM $Ca^{++}$ KGM bulletKit medium (Clonetics) with 30 μg/ml bovine pituitary extract. For experiments, pituitary extract was omitted from media of TGF-β1-treated and untreated control keratinocyte cultures.

For treatment with TGF-β1 (Austral Biologicals), just-confluent cells were rinsed once with serum- or pituitary extract-free media and then treated with vehicle (5 mM HCl) or TGF-β1. Unless otherwise noted, TGF-β1 treatment was 2 ng/ml for MG-63 cells and 10 ng/ml for other cell types. Also, unless otherwise noted, TGF-β1 treatments were 24 h for cultures harvested for RNA, and 48 h for cultures harvested for proteins. Ascorbate treatment of cells was at 50 μg/ml.

Northern Blots

A 471-bp probe for RNA sequences shared by human BMP-1 and mTld has been described (4). The 1474-bp insert of full-length human cDNA clone KT11 (16) was used as a probe for PCPE RNA. Probe for PNP was an 802 base pair fragment of human PNP cDNA that corresponds to, but differs in size from, the fragment between nucleotides 459–1266 of the published bovine cDNA sequence (47). The human PNP probe fragment can be amplified using primers that correspond to bases 459–480 and 1243–1266 of the bovine sequence described in (47). Probe for human α1(I) collagen RNA was a 4.3 kb EcoRI fragment from plasmid pHUC (17), and a 2.0 kb human β-actin probe was purchased (Clontech). Poly($A^+$) RNA was prepared with the FastTrack kit (Invitrogen). 2 μg poly($A^+$) RNA per lane was electrophoresed on 1.2% agarose, 2.2 M formaldehyde gels, and transferred to Hybond-N+ membranes (Amersham). Probes were radiolabeled to a specific activity of 4–6×$10^9$ cpm/μg by random priming (18) and hybridized to blots in QuikHyb (Stratagene) at 65° C. for 1 h. Blots were washed twice in 2×SSC, 0.1% SDS for 10 min at room temperature, then twice in 0.1×SSC, 0.1% SDS for 20 min at 65° C., and exposed to Kodak X-Omat AR film with intensifying screens at −70° C. Autoradiograms were quantitated by scanning densitometry (Biomed Instruments) of autoradiograms exposed for varying lengths of time.

Antibodies

All antibodies were derived from polyclonal rabbit antisera. Antisera LF-40, LF-41, and LF-67 for the human proα1(I) N- and C-propeptides and C-telopeptide, respectively, have been described (19).

To raise antibodies to full-length PCPE, sample enriched for 55 kDa PCPE by lysyl-Sepharose chromatography (10) was subjected to SDS-PAGE in unreduced 10% gels, and proteins were visualized with Coomassie blue (20). The 55 kDa PCPE band was excised, equilibrated with SDS sample buffer (21) with 100 mM dithiothreitol, and electrophoresed on a 7% gel. After staining, gel pieces containing 55 kDa PCPE were equilibrated with PBS, crushed, and used for immunization as described (10). PCPE antibodies, isolated from an IgG fraction by adsorption to 55 kDa PCPE bound to nitrocellulose (22), were eluted with 5 mM glycine, 0.5 M NaCl, 0.1% BSA (pH 2.3) and neutralized with 1 M $Na_2HPO_4$.

Antibodies to the C-termini of BMP-1 and mTld were raised against peptides CPHQLKFRVQKRNRTPQ (SEQ ID NO: 1) and CLRYTSTKFQDTLHSRK (SEQ ID NO: 2), representing the final 16 residues of each respective protein plus an additional cysteine for coupling to keyhole limpet hemocyanin (KLH). Rabbits injected with the mTld peptide were boosted with the same peptide conjugated to ovalbumin to increase titers. BMP-1/mTld proregion antibodies were raised against peptide DLAEEDDSEPLNYKDPC (SEQ ID NO: 3), that corresponds to residues 31–47 of the BMP-1 sequence (1), linked to KLH. Peptide antibodies were affinity-purified on columns of the appropriate peptide coupled to TC gel (Quality Controlled Biochemicals) via the cysteine thiol. They were eluted with 3 M $MgCl_2$, 25% ethylene glycol and dialyzed against 10 mM sodium phosphate (pH 7.4), 20 mM NaCl.

Western Blots

Protease inhibitors (2.5 mM EDTA, 1 mM phenylmethylsulfonyl fluoride, 1 mM p-aminobenzoic acid, 1 mM N-ethylmaleimide) were added to harvested media and proteins were precipitated by adding trichloroacetic acid to 10%. Pellets were washed with ice-cold acetone, then washed twice with 75% ethanol, 12.5 mM Tris (pH 7.5), dried and resuspended in SDS sample buffer with 5% β-mercaptoethanol. Cell layers were scraped into hot SDS sample buffer, as described (23). Media and cell layer samples, equivalent to 5×$10^5$ fibrogenic cells or keratinocytes per lane, were subjected to SDS-PAGE and transferred to Immobilon-P membranes (Millipore) by electroblotting in 25 mM Tris, 192 mM glycine, 10% methanol at 4°

C. Blots were incubated ~14 h with primary antibody diluted 1:5000 in PBS, 1% BSA, 0.05% Tween-20. After washing three times with wash buffer (PBS, 0.05% Tween-20), blots were incubated 1 h with horseradish peroxidase-conjugated donkey anti-rabbit IgG (Amersham) diluted 1:4000. Blots were then washed four times with wash buffer, incubated with SuperSignal CL-HRP substrate (Pierce), and exposed to film. Apparent molecular weights of bands were estimated by comparison to electrophoretic mobilities of prestained standards (Bio-Rad).

To quantitate relative amounts of BMP-1, gel lanes were loaded with sample corresponding to the medium of $2.5 \times 10^5$ untreated MG-63 cells or to the media of $1.25 \times 10^4$, $5.0 \times 10^4$, or $2.5 \times 10^5$ TGF-$\beta$1-treated MG-63 cells. After SDS-PAGE a blot was prepared, treated with antibody to the BMP-1 C-terminus (as above), and then incubated with $^{125}$I-labeled protein A (Amersham) for 1 h in PBS, 1% BSA, 0.05% Tween-20, 1 mM dithiothreitol. The blot was washed 8 h with wash buffer, exposed to film and the autoradiograph used as a template for excising radioactive BMP-1 bands which were counted in an A 800CD $\gamma$ counter (Packard).

For digestion with peptide-N-glycosidase F (PNGase F), proteins were precipitated from media with trichloroacetic acid (as above); denatured in 0.5% SDS, 1% $\beta$-mercaptoethanol 10 min at 100° C.; incubated 1 h at 37° C. with 500 units PNGase F (New England Biolabs) in 50 mM sodium phosphate (pH 7.5), 0.1% SDS, 1% NP-40, 1 mM phenylmethylsulfonyl fluoride, 100 $\mu$g/ml soybean trypsin inhibitor, 10 mM benzamidine; and the reaction stopped by adding 4×SDS sample buffer and heating 4 min at 100° C.

In Vitro Procollagen Cleavage Assays

Media tested for PCP activity contained 1 mM each phenylmethylsulfonyl fluoride, p-aminobenzoic acid, and N-ethylmaleimide; was concentrated 50-fold in Centriprep concentrators (Amicon); and then dialyzed against 50 mM Tris-HCl, 0.15 NaCl, 5 mM CaCl$_2$. 5 $\mu$l concentrated medium was added to 0.125 $\mu$g $^{14}$C procollagen substrate from chick embryo tendon cultures in 5 $\mu$l 0.1 M Tris-HCl, 0.1 M NaCl, 5 mM CaCl$_2$, 0.02% Brij 35 (pH 7.6), and incubated 4 h at 35°20 C. Reactions were stopped by adding 5 $\mu$l 3×SDS sample buffer and heating 4 min at 100° C. prior to SDS-PAGE on nonreduced 6% gels. Gels were fixed in 20% MeOH, placed in Amplify (Amersham) 30 min, dried and exposed to film.

To quantitate PCP activity, percent cleavage was calculated for each lane of an autofluorogram by comparing signal remaining in the pro$\gamma$ band (procollagen in which cleavage has not occurred in any of the three PCP cleavage sites) to total signal (pro$\gamma$+pro$\beta$+pro$\alpha$+pN$\alpha$1+$\alpha$1+pN$\alpha$2+$\alpha$2+free C-propeptide bands). Percent cleavages achieved with media from cultures treated with TGF-$\beta$1, ascorbate, or TGF-$\beta$1 plus ascorbate were then compared to percent cleavage achieved with media from untreated controls to calculate fold increases in PCP activity. Signals on autofluorograms were quantitated with an IS1000 Digital Video Imaging System (Alpha Innotech).

RNase Protection Assays

To generate BMP-1/mTld-specific riboprobe, a 1,619 bp ApaI-EagI fragment was excised from a baculovirus transfer vector containing full-length human BMP-1 cDNA (6). The fragment, extending from nucleotide 615 of the BMP-1 cDNA sequence (1) to an EagI site in the vector polylinker, was inserted between pBluescript II KS+ (Stratagene) ApaI and EagI sites, and linearized at a HincII site at nucleotide 1655 of the BMP-1 sequence (1). This template produced a 617-base riboprobe of which 575 bases are BMP-1-specific and 481 bases are specific for alternatively spliced mTld RNA. For PCPE-specific riboprobe, a 329 bp fragment of PCPE cDNA clone KT3 (16) was excised with EcoRI and SacII and inserted between pBluescript II KS+EcoRI and SacII sites. This template, linearized at the pBluescript XhoI site, produced a 391-base riboprobe, 329 bases of which correspond to nucleotides 557 to 885 of the human PCPE cDNA sequence (16). Control riboprobe was generated with template pTRI-$\beta$-actin-Human (Ambion). Uniformly $^{32}$P-labeled riboprobes were generated by transcription with RNA polymerase T7, hybridized to total RNA isolated with TRIzol (GIBCO), and analyzed by digestion with RNases A and T1 and electrophoresis on 6% denaturing gels, as described (24).

Results

TGF-$\beta$1 Selectively Increases Levels of BMP-1 and mTld, but not PCPE, mRNA in MG-63 Osteosarcoma Cells To determine whether levels of PCPE, BMP-1 and/or mTld mRNA are influenced by treatment with TGF-$\beta$, just-confluent MG-63 cultures were treated 24 h with 2 ng/ml TGF-$\beta$1. Levels of the ~3.0 kb BMP-1 mRNA and ~5.5 and ~4.1 kb mTld mRNAs (4), were all increased by TGF-$\beta$1 treatment. Interestingly, mRNAs for the two proteins did not increase to the same extent, with BMP-1 mRNA increasing ~7 fold and both mTld mRNA forms increasing only ~4 fold. By comparison, levels of the 4.8 and 5.8 kb pro$\alpha$1(I) collagen mRNAs (25) increased ~9 fold while those of the $\beta$-actin mRNA control did not change. In contrast to the induction of BMP-1 and mTld mRNA, levels of PCPE mRNA were not increased by TGF-$\beta$1.

Incubation of MG-63 cells with TGF-$\beta$1 concentrations ranging from 0.01 to 10 ng/ml, showed induction of BMP-1 and mTld mRNAs to be dose-dependent, with substantial increases first noted at 0.5 ng/ml and maximum induction at 2 ng/ml. Induction of mTld and BMP-1 mRNAs was somewhat less at 10 ng/ml than at 2 ng/ml, possibly due to toxicity of TGF-$\beta$1 at higher concentrations (26). When kinetics of induction of BMP-1/mTld mRNAs were examined by incubating MG-63 cultures in 2 ng/ml TGF-$\beta$1 for varying times, substantial increases first occurred at 12 h, with maximal levels attained at 24 h post-treatment. Thus, induction was delayed compared to induction of RNAs encoding a variety of extracellular matrix proteins, which generally occurs within 3–5 h of TGF-$\beta$1 treatment of various cell types (13). This delay suggested that induction of BMP-1/mTld mRNAs may occur secondarily to an earlier event triggered by TGF-$\beta$1, a possibility supported by experiments in which treatment of confluent cultures with cycloheximide prior to TGF-$\beta$1-treatment showed protein synthesis to be required prior to induction of BMP-1/mTld mRNAs.

Levels of Secreted BMP-1 and mTld, but not PCPE, are Upregulated by TGF-$\beta$1 in Fibrogenic Cell Cultures To determine whether induction of steady state levels of BMP-1 and mTld mRNA in MG-63 cells was paralleled by increases in the cognate proteins, levels of BMP-1 and mTld protein secreted into culture media were examined by Western blots. Antibodies specific for the BMP-1 C-terminus detected bands of ~88 kDa and ~77 kDa, both of which were strongly upregulated by TGF-$\beta$1. Antibody to the mTld C-terminus detected a ~130 kDa band that was upregulated by TGF-$\beta$1 to a lesser extent than the anti-BMP-1-reactive bands. The relative extent of induction of BMP-1-and mTld-specific bands, thus appeared similar to the relative extent of induction of the cognate mRNAs.

To quantitate the induction of secreted BMP-1, Western blots were incubated with antibody to the BMP-1

C-terminus and then with $^{125}$I-protein A, to allow subsequent excision and quantitating of counts in BMP-1 bands. This method, which can provide good quantitation of relative amounts of proteins (27), showed levels of the 88 kDa BMP-1 band to be ~8-fold higher in TGF-β1-treated MG-63 cultures than in untreated cultures. Thus, the level of induction of secreted BMP-1 was similar to the level of induction of cognate mRNA. The 77 kDa band was not detected on these blots and was determined to be unrelated to BMP-1 (see below).

Ascorbate may stimulate production of type I procollagen at transcriptional and posttranscriptional levels (28–30). Since we were interested in mechanisms which might contribute to co-expression of BMP-1 and type I procollagen, we examined whether levels of BMP-1 were also upregulated by ascorbate. Although the intensity of BMP-1 and mTld protein bands did not appreciably increase in the presence of ascorbate alone, intensities seemed somewhat higher in the presence of TGF-β1 plus ascorbate than in the presence of TGF-β1 alone. In contrast to BMP-1 and mTld, levels of secreted PCPE did not increase in MG-63 cultures treated with TGF-β1, ascorbate, or ascorbate plus TGF-β1. Thus, as with BMP-1 and mTld, levels of secreted PCPE paralleled levels of cognate mRNA.

To ascertain whether results like those obtained with MG-63 cells were common to other fibrogenic cells, analyses were done on MC3T3-E1 osteoblastic mouse cells and human dermal fibroblasts. Results obtained with these cells were similar to those observed with MG-63 cells, in that levels of secreted BMP-1 and mTld were elevated in the presence of TGF-β1 and appeared to be slightly more elevated in the presence of TGF-β1 plus ascorbate. As with MG-63 cells, levels of PCPE were not dramatically changed in a consistent way by addition of TGF-β1 and/or ascorbate.

Some Western blots using BMP-1 C-terminus antibody detected a ~77 kDa band, in addition to the 88 kDa BMP-1 band, in MG-63 media. This band, without counterpart in MC3T3-E1 or fibroblast cultures, was not always detected in MG-63 cultures treated with TGF-β1 or TGF-β1 plus ascorbate and was absent upon culturing in the presence of 0.1% serum or when protein A was used instead of secondary antibody. The 77 kDa MG-63 band was detected on blots when preimmune sera or mTld C-terminus antibody was used as primary antibody, and by secondary antibody in the absence of primary antibody (not shown). We thus conclude that the 77 kDa MG-63 band is unrelated to BMP-1.

Cleavage of Endogenous Type I Procollagen C- and N-propeptides is Induced in MG-63 Cultures by TGF-β1 Plus Ascorbate We next examined whether induction of secreted BMP-1 and mTld in MG-63 cultures was paralleled by induction of PCP activity, as evidenced by increased cleavage of endogenous type I procollagen C-propeptides. Immunoblots using antibody to the proα1(I) N-propeptide did not detect pNα1 (I) chains in media of untreated cells or, surprisingly, in media of cells treated with TGF-β1 alone, even though the latter contained relatively high levels of procollagen, BMP-1 and mTld. In contrast, pNα1(I) chains were found in media of ascorbate-treated cells, in a proα1(I) to pNα1(I) ratio of ~1.0:0.3, and at higher levels in media of cells treated with TGF-β1 plus ascorbate, with a proα1(I) to pNα1(I) ratio of ~1.0:0.8.

Proα1(I) C-telopeptide antibody, capable of detecting α1(I), pNα1(I), and pCα1(I) chains revealed relative levels of proα1(I) and pNα1(I) chains in the various media, similar to those detected by the first antibody. In addition, pCα1(I) and mature α1(I) chains were detected in media of cells treated with TGF-β1 plus ascorbate. In the latter sample, the ratio of unprocessed proα1(I) chains to chains from which the C-propeptide had been cleaved [pNα1(I)+α1(I)] was ~1.0:2.7, a value ~10-fold greater than the proα1(I) to pNα1(I) ratio (~1.0:0.3) detected in the ascorbate treated sample by the same antibody. Thus, although cultures treated with TGF-β1 plus ascorbate contained substantially more substrate than cultures treated with ascorbate alone, a greater fraction had undergone removal of C-propeptides, indicating significantly increased PCP activity.

The appearance of quantities of pCα1(I) and α1(I) chains only in media of MG-63 cells treated with TGF-β1 plus ascorbate, indicated that procollagen N-proteinase (PNP) activity is also elevated under these conditions. Highlighting this induction, proα1(I) C-propeptide antibody detected pCα1(I) chains only in media of cells treated with TGF-β1 plus ascorbate. Northern blot analysis confirmed that the approximately 8 kb PNP mRNA was upregulated about 9-fold in similarly treated duplicate MG-63 cultures. Since the N-propeptides of procollagens I and III are cleaved by two different PNP enzymes (31,32), and since MG-63 cells produce procollagen III (33), Western blots using antibody against the type III procollagen C-propeptide were performed and showed that procollagen III PNP activity is also elevated in the presence of TGF-β1 plus ascorbate.

Since procollagen processing may help regulate incorporation of monomers into fibrils (34), levels of processed α1(I) chains incorporated into MG-63 cell layers were also examined. Consistent with results obtained from media, C-telopeptide antibody found high levels of α1(I) chains in cell layers treated with TGF-β1 plus ascorbate, while untreated cell layers or cell layers treated with TGF-β1 alone did not contain detectable α1(I). Cell layers treated with ascorbate or with ascorbate plus TGF-β were enriched for α1(I) chains compared to media from the same cultures. This enrichment may reflect preferential incorporation of mature monomers into growing fibrils, rather than increased processing in cell layers compared to media. Consistent with this likelihood, pNα1(I), but not pCα1(I), chains were found in cell layers treated with ascorbate or with TGF-β1 plus ascorbate, appearing to confirm results previously obtained with in vitro fibrillogenesis systems (34), suggesting that pNα1(I) but not pCα1(I) chains are incorporated into growing fibrils.

PCP and PNP Activity Against Exogenous Procollagen Substrate is Increased in Media of TGF-β1-treated MG-63 Cultures It seemed paradoxical that although secreted BMP-1 and mTld were elevated to only slightly higher levels in MG-63 cultures treated with TGF-β1 plus ascorbate than in cultures treated with TGF-β1 alone, processing of endogenous procollagen was detectable only in the former. Thus, to examine whether differences in endogenous substrate might contribute to differences observed in levels of processing, MG-63 media were assayed for PCP and PNP activity using exogenous radiolabeled procollagen substrate. As with endogenous substrate, PCP and PNP activities against exogenous substrate were highest in media of cells treated with TGF-β1 plus ascorbate, as evidenced by generation of mature α-chains, processing intermediates, and free C-propeptides. However, in contrast to results with endogenous substrate, PCP and PNP activities against exogenous substrate were increased in media of cells treated with TGF-β1 alone, to levels approaching those of cultures treated with TGF-β1 plus ascorbate. Thus, in seven independent experiments, the mean increase of PCP activity against exogenous substrate was 2.4 (±0.2)-fold for cultures treated with TGF-β1 plus ascorbate, and 1.7 (±0.1)-fold for cultures treated with TGF-β1 alone (values are mean ±S.E). PCP activity in media of cultures treated with ascorbate alone was virtually unchanged, 1.0 (±0.1)-fold, compared to untreated controls. These results suggest that large differences in processing of endogenous substrate in cultures treated with TGF-β1 alone, compared to cultures treated with TGF-β1 plus ascorbate, were at least partly due to differences in the hydroxylation state and conformation of the substrate.

Most BMP-1 and mTld Secreted by Fibrogenic Cells in Response to TGF-β1 is Processed to Mature, Active Forms Proteases of the astacin family are synthesized as proenzymes with N-terminal proregions that must be removed for activation (36,37). Thus, the lesser induction of PCP activity against exogenous substrate (~1.7 fold for TGF-β1-treated cultures), relative to levels of induction of secreted BMP-1 detected by quantitative Western blots (~8-fold for TGF-β1-treated cultures), might have been due to secretion of most BMP-1 and mTld, as inactive precursors. To ascertain whether this was the case, antibody to proregion sequences common to BMP-1 and mTld precursors was prepared and used to examine immunoblots of MG-63 media samples. This antibody did not recognize the major 88 kDa BMP-1 band, but did recognize a ~101 kDa band that also appears as a minor band on immunoblots using the BMP-1 C-terminus antibody. Thus, although a small proportion is unprocessed, the majority of TGF-β1-induced BMP-1 secreted by the fibrogenic cells is in the processed active form. In addition, the proregion antibody did not recognize the ~130 kDa band detected by mTld C-terminus antibody, but did recognize a ~143 kDa band. Thus, the majority of mTld secreted by TGF-β1-treated fibrogenic cells is also processed to the mature form, while a small proportion, at levels undetectable with the mTld C-terminus antibody, is unprocessed. Interestingly, in repeated experiments, media of MG-63 cells treated with TGF-β1 alone consistently had lesser amounts of activated, and greater amounts of unprocessed, BMP-1 and mTld than did cultures treated with TGF-β1 plus ascorbate. Thus, additional processing of BMP-1 and mTld into mature forms seems to occur in the presence of ascorbate, perhaps accounting for the higher levels of PCP activity against exogenous substrate in media of cultures treated with TGF-β1 plus ascorbate, than in media of cultures treated with TGF-β1 alone.

Previously, recombinant human BMP-1 produced in a baculovirus system by this laboratory, was shown to have high PCP activity and to be processed to the mature form (6). Thus, BMP-1 secreted by TGF-β1-treated fibrogenic cells should have the same electrophoretic mobility as the recombinant BMP-1, if in an active processed form. Electrophoretic mobilities of BMP-1 from TGF-β1-treated fibroblast media and from the baculovirus system were compared after treatment of samples with PNGase F to control for mobility differences due to differences in Asn-linked glycosylation between insect and mammalian cells (6,38). Upon removal of Asn-linked carbohydrates, the major form of BMP-1 secreted by TGF-β1-treated fibroblasts had the same mobility as recombinant active BMP-1, bolstering the conclusion that most BMP-1 secreted by fibrogenic cells in response to TGF-β1 is processed to the mature form.

The Major Secreted Product of the BMP1 gene in TGF-β1-treated Human Keratinocytes is Unprocessed mTld It was of interest to determine whether the patterns of expression and regulation of BMP-1 and mTld described above, are also found in non-fibrogenic cells. Keratinocytes were chosen for study since they do not produce readily detectable fibrillar collagens, but do appear to utilize BMP-1 and/or mTld for processing laminin 5 (12). Consistent with previous reports that keratinocytes do not produce type I collagen (39), type I collagen was not detected in media of keratinocytes treated or untreated with TGF-β1 and/or ascorbate, by Western blots using proα1(I) N-propeptide, C-propeptide, or C-telopeptide antibodies (not shown). In addition, and in contrast to results obtained with fibrogenic cells, PCPE expression by keratinocytes was undetectable by Western blot, regardless of culture conditions. Also in contrast to results with fibrogenic cells, antibodies against BMP-1 or mTld C-termini did not clearly detect specific bands on Western blots of media samples from keratinocytes treated or untreated with TGF-β1 and/or ascorbate. This indicated that if keratinocytes secrete BMP-1 and/or mTld, then steady state levels in media are significantly lower than in fibrogenic cell media.

We had noted in previous experiments that the proregion antibody was of higher affinity than antibodies against the C-termini of BMP-1 and mTld. The proregion antibody was able to detect ~143 kDa and ~101 kDa bands, corresponding in size to unprocessed mTld and BMP-1 bands observed in MG-63 cultures, in media of keratinocytes treated with TGF-β1 or with TGF-β1 plus ascorbate. The ~143 kDa band was barely detectable, and the ~101 kDa band was not detected, in media of untreated or ascorbate-treated keratinocytes. Consistent with the observation that keratinocytes secrete predominantly unprocessed mTld and BMP-1 in response to TGF-β1, PCP activity against exogenous procollagen substrate was at very low levels in media of keratinocytes treated or untreated with TGF-β1 and/or ascorbate.

An RNase protection assay showed keratinocytes and MG-63 cells to contain comparable levels of mTld RNA, but MG-63 cells contained higher levels of BMP-1 RNA. Thus, secretion of predominantly mTld by keratinocytes and predominantly BMP-1 by MG-63 cells is reflected, at least in part, in levels of cognate RNA transcripts. RNase protection also demonstrated that absence of PCPE secretion by keratinocytes is reflected in a virtual absence of PCPE RNA.

Discussion

We have demonstrated that TGF-β1 elevates levels of BMP-1 and mTld in fibrogenic cells and keratinocytes. PNP activity against procollagens I and III and PNP mRNA was also elevated by TGF-β1 in fibrogenic cells. Thus, in addition to increasing the deposition of matrix through induction of matrix components, lysyl oxidase, and metalloprotease inhibitors; TGF-β1 also influences net matrix deposition by inducing the proteases which process procollagens, laminin 5, and lysyl oxidase into mature forms.

The induction of BMP-1 and mTld by TGF-β1, described here, is particularly intriguing in the context of previous suggestions that BMP-1- and tolloid-like proteins may activate TGF-β-like molecules (1–3). TGF-β1 is itself secreted as a latent form (40) and the possibility, therefore, exists of a positive feedback loop in which BMP-1, mTld and/or PNP activate, and are in return induced by, TGF-β1. There is a precedent for such positive feedback loops in matrix deposition, since the effects of TGF-β1 on matrix deposition are amplified and prolonged through autoinduction by TGP-β1 of its own expression (41). Preliminary studies with recombinant proteins suggest that BMP-1 may indeed be capable of directly activating TGF-β1 small latent complex.

Removal of the proregion from astacin-like proenzymes is thought necessary for the production of active forms of these enzymes (37). Thus, persistence or removal of the proregion represents another potential control point for regulating BMP-1 and mTld activities. The degree of processing of secreted BMP-1 and mTld is shown herein to be cell type-specific, with predominantly processed forms produced by TGF-β1-treated fibrogenic cells and predominantly unprocessed forms produced by TGF-β1-treated keratinocytes. Clearly, the production of large amounts of activated BMP-1 and mTld would aid fibrogenic cells in their highly specialized roles of producing large quantities of fibrillar collagen matrix, especially in response to TGF-β. It is less clear why keratinocytes produce predominantly unprocessed, inactive forms of mTld and BMP-1 in response to TGF-β. Consistent with this finding, however, is the observation that processing of 72, the laminin 5 chain cleaved by mTld and/or BMP-1, is delayed following secretion by cultured keratinocytes (12). Thus, extracellular processing of mTld and BMP-1 may be a rate-limiting step in the deposition of keratinocyte extracellular matrix, of which laminin 5 is a major component (42,43). In vivo, such processing may be regulated by epithelial-mesenchymal interactions that influence the production of matrix by basal keratinocytes (44). Keratinocytes were found not to produce detectable amounts of PCPE, suggesting that PCPE may not play a role in laminin 5 processing. However, the possibility that, in vivo, PCPE may be provided by dermal fibroblasts for this purpose has not been precluded.

Interestingly, the relative amounts of BMP-1 and mTld produced by cells were also found to be cell type-specific: fibrogenic cells produced relatively large amounts of BMP-1, while keratinocytes produced predominantly mTld, at both RNA and protein levels. Possible functional significance for the production of differing ratios of BMP-1 and mTld by different cell types remains to be determined, however, since a functional difference has yet to be discerned for these two protein products of the same gene.

Previously, the low levels of PCP activity detectable in tissues and in cell culture systems have led to suggestions that the enzyme is either secreted as an inactive precursor or is co-expressed with an endogenous inhibitor (8). Either of these possibilities might have explained the discrepancy observed in the present study between the induction by TGF-β1 in MG-63 cultures of an ~8-fold increase in secreted BMP-1 and a ~2-fold increase in media PCP activity against exogenous substrate. However, since secreted BMP-1 and mTld were both found predominantly as processed forms, this leaves the interesting possibility of an endogenously produced inhibitor. Previously, localized control over the activities of various proteases, including degradative matrix metalloproteases such as stromelysins and collagenases, has been shown to involve not only the processing of proenzymes to mature forms, but also the balance between levels of activated enzyme and levels of specific inhibitors co-expressed by the same cell types (45). Studies to determine the possible existence of inhibitors for BMP-1, mTld, and related proteases (46), seem warranted by results presented in the current study. Clearly, such inhibitors, should they exist, could play roles in morphogenetic processes as important as those of the proteases with which they interact.

A final point of interest relates to the observed processing of endogenous procollagen in MG-63 cultures treated with TGF-β1 plus ascorbate and the absence of such processing in cultures treated with TGF-β1 alone. Both cultures secreted high levels of similarly processed BMP-1 and mTld. Moreover, the TGF-β1 plus ascorbate-treated cultures had only slightly higher PCP activity against exogenous substrate, corresponding to a slightly higher ratio of activated to unprocessed BMP-1. The most straightforward interpretation of these data is that fully hydroxylated procollagen produced by ascorbate-treated cultures, or supplied as exogenous substrate, is much better substrate for BMP-1 than is underhydroxylated procollagen produced in the absence of ascorbate. Since underhydroxylated procollagen is not likely to be in a compact triple helical form at 37° C. (35), these data provide the first indication of a conformational requirement for the cleavage of procollagen by PCP. This is in contrast to an earlier report (8) that found PCP to cleave heat denatured procollagen with about the same efficiency as native procollagen.

Working Embodiment of Assay Performed in Accordance with Invention

From the foregoing, it is apparent that active procollagen-cleaving enzymes can be produced by, and secreted in high quantity from, fibrogenic cells after induction and that the activity of those enzymes can be assessed immunologically. This provides a basis for an assay of compounds that can modulate the activity of these enzymes. The following example demonstrates the utility of such an assay.

MG-63 human osteosarcoma cells were maintained in Dulbecco's modified Eagle's medium with 10% heat-inactivated (30 min, 55° C.) fetal calf serum (FCS). For experiments in which samples for immunoblots were prepared from MG-63 cultures, media was serum free. For treatment with TGF-β1 (Austral biologicals), just-confluent cells were rinsed once with serum-free media and then treated with 2 ng/ml TGF-β1 and 50 μg/ml ascorbate for 48. Potential inhibitors were added at the same time as TGF-β at concentrations of 5, 20, or 50 μM. Cells were changed to fresh media containing TGF-β, ascorbate and potential modulators at 24 h. LF-67 antibodies used for the immunoblots were derived from polyclonal rabbit antisera, are specific for sequences within the C-telopeptide domain of the proα1(I) collagen chain, and have been described previously (19).

Western Blots

Protease inhibitors (2.5 mM EDTA, 1 mM phenylmethylsulfonyl fluoride, 1 mM p-aminobenzoic acid, 1 mM N-ethylmaleimide) were added to harvested media and proteins were precipitated by adding trichloroacetic acid to 10%. Pellets were washed with ice-cold acetone, then washed twice with 75% ethanol, 12.5 mM Tris (pH 7.5), dried and resuspended in SDS sample buffer with 5% β-mercaptoethanol. Cell layers were scraped into hot SDS sample buffer, as described (23). Samples, equivalent to the media of $5 \times 10^5$ cells per lane, were subjected to SDS-PAGE and transferred to Immobilon-P membranes (Millipore) by electroblotting in 25 mM Tris, 192 mM glycine, 10% methanol at 4° C. Blots were incubated ~14 h with primary antibody diluted 1:5000 in PBX, 1% BSA, 0.05% Tween-20. After washing three times with wash buffer (PBS, 0.05% Tween-20), blots were incubated 1 h with horseradish peroxidase-conjugated donkey anti-rabbit IgG (Amersham) diluted 1:4000. Blots were then washed four times with wash buffer, incubated with SuperSignal CL-HRP substrate (Pierce), and exposed to film.

Duplicate plates of cells grown under conditions with or without potential modulators were either processed for Western blot analysis of processing or were counted and tested for trypan blue exclusion to test for possible toxicity of each potential modulator.

Three potential modulating compounds were tested. One was toxic to cells at all concentrations tested. Two other compounds were found to be inhibitory to procollagen C-proteinase activity as evidenced by the disappearance of certain proα1(I) collagen processing intermediates (e.g. α1(I) and pNα1(I) forms) in media and cell layers—without the disappearance or diminution of secreted proα1(I) chains. Some toxicity was found for one of the compounds only at relatively high (e.g. 50 μM) concentrations, as evidenced by a small decrease in cell numbers and by a decrease in the amount of proα1(I) chains.

The present invention is not to be limited by the foregoing but rather should encompass all such variations and modifications as come within the scope of the following claims.

REFERENCES

1. Wozney, J. M., Rosen, V., Celeste, A. J., Mitsock, L. M., Whitters, M. J., Kriz, R. W., Hewick, R. M., and Wang, E. A (1988) *Science* 242, 1528–1534
2. Childs, S. B., and O'Connor, M. B. (1994) *Dev. Biol.* 162, 209–220
3. Finelli, A. L., Bossie, C. A., Xie, T., and Padgett, R. W. (1994) *Development* 120, 861–870
4. Takahara, K., Lyons, G. E., and Greenspan, D. S. (1994) *J. Biol. Chem.* 269, 32572–32578
5. Prockop, D. J., and Kivirikko, K. I. (1995) *Annu. Rev. Biochem.* 64, 403–434
6. Kessler, E., Takahara, K., Biniaminov, L., Brusel, M., and Greenspan, D. S. (1996) *Science* 271, 360–362
7. Li, S.-W., Sieron, A. L., Fertala, A., Hojima, Y., Arnold, W. V., and Prockop, D. J. (1996) *Proc. Natl. Acad. Sci. U.S.A.* 93, 5127–5130
8. Hojima, Y., van der Rest, M., and Prockop, D. J. (1985) *J. Biol. Chem.* 260, 15996–16003
9. Kessler, E., Adar, R., Goldberg, B., and Niece, R. (1986) *Collagen Rel. Res.* 6, 249–266
10. Kessler, E. and Adar, R. (1989) *Eur. J. Biochem.* 186, 115–121
11. Panchenko, M. V., Stetler'Stevenson, W. G., Trubetskoy, O. V., Gacheru, S. N., and Kagan, H. M. (1996) *J. Biol. Chem.* 271, 7113–7119
12. Amano, S., Takahara, K., Gerecke, D., Nishiyama, T., Lee, S., Greenspan, D.S., and Burgeson, R. E. (1996) *Mol. Biol. Cell* 7, Suppl., 58a (Abstr. 338)
13. Massagué, J. (1990) *Annu. Rev. Cell Biol.* 6, 597–641
14. Feres-Filho, E. J., Young, J. C., Han, X., Takala, T. E. S., and Trackman, P. C. (1995) *J. Biol. Chem.* 270, 30797–30803
15. Korang, K., Christiano, A. M., Uitto, J., and Mauviel, A. (1995) *FEBS Lett.* 368, 556–558
16. Takahara, K., Kessler, E., Biniaminov, L., Brusel, M., Eddy, R. L., Jani-Sait, S., Shows, T. B., and Greenspan, D. S. (1994) *J. Biol. Chem.* 269, 26280–26285
17. Stacey, A., Mulligan, R., and Jaenisch, R. (1987) *J. Virol.* 61, 2549–2554
18. Feinberg, A. P., and Vogelstein, B. (1984) *Anal. Biochem.* 137, 266–267
19. Fisher, L. W., Stubbs, J. T. III, and Young, M. G. (1995) *Acta Orthop Scand (Suppl* 266) 66, 61–65
20. Hunkapiller, M. W., Lujan, E., Ostrander, F., and Hood, L. E. (1983) *Methods Enzymol.* 91, 227–236
21. Laemmli, U. K. (1970) *Nature* 227, 680–685
22. Harlow, E., and Lane, D. (1988) *Antibodies: A Laboratory Manual,* Cold Spring Harbor Laboratory, Cold Spring Harbor, N.Y.
23. Sambrook, J., Fritsch, E. F., and Maniatis, T. (1989) *Molecular Cloning: a Laboratory Manual,* 2nd ed., Cold Spring Harbor Laboratory, Cold Spring Harbor, N.Y.
24. Greenspan, D. S., Lee, S.-T., Lee, B. S., and Hoffman, G. G. (1991) *Gene Expression* 1, 29–39
25. Chu, M.-L., de Wet, W., Bernard, M., and Ramirez, F. (1985) *J. Biol. Chem.* 260, 2315–2320
26. Lawrence, R., Hartmann, D. J., and Sonenshein, G. E. (1994) *J. Biol. Chem.* 269, 9603–9609
27. Howe, J. G., and Hershey, J. W. B. (1981) *J. Biol. Chem.* 256, 12836–12839
28. Lyons, B. L., and Schwarz, R. I. (1984) *Nucleic Acids Res.* 12, 2569–2579
29. Geesin, J. C., Darr, D., Kaufman, R. Murad, S., and Pinnell, S. R. (1988) *J. Invest. Dermatol.* 90, 420–424
30. Chan, D., Lamade, S. R., Cole, W. G., and Bateman, J. F. (1990) *Biochem. J.* 269, 175–181
31. Halila, R., and Peltonen, L. (1986) Biochem. J. 239, 47–52
32. Colige, A. Beschin, A., Samyn, B., Goebels, Y., Van Beeumen, J., Nusgens, B. V., and Lapière, C.M. (1995) *J. Biol. Chem.* 270, 16724–16730
33. Franceschi, R. T., Romano, P. R., and Park, K.-Y. (1988) *J. Biol. Chem.* 263, 18938–18945
34. Prockop, D. J. and Hulmes, D. J. S. (1994) in *Extracellular Matrix Assembly and Structure* (Yurchenco, P. D., Birk, D. E. and Mechan, R. P., eds) pp. 47–90, Academic Press, Inc., New York
35. Prockop, D. J., Berg, R. A., Kivirikko, K. I., and Uitto, J. (1976) in *Biochemistry of Collagen* (Ramachandran, G. N. and Reddi, A. H., eds) pp. 163–273, Plenum Press, New York
36. Bond, J. S., and Beynon, R. J. (1995) *Protein Sci.* 4, 1247–1261
37. Bode, W., Gomis-Rüth, F. X., Huber, R, Zwilling, R., and Stöcker, W. (1992) *Nature* 358, 164–167
38. Jarvis, D. L., and Summers, M. D. (1992) in *Recomnbinant DNA Vaccines: Rationale and Strategies* (Isaacson, R. E., ed) pp. 265–291, Dekker, New York
39. Ryynanen, J., Sollberg, S., Olsen, D. R., and Uitto, J. (1991) *Biochem. Biophys. Res. Commun.* 180, 673–680
40. Lawrence, D. A., Pircher, R., Kryceve-Martinerie, C., and Jullien, P. (1984) *J. Cell. Physiol.* 121, 184–188
41. Van Obberghen-Schilling, E., Roche, N. S., Flanders, K. C., Sporn, M. B., and Roberts, A. B. (1988) *J. Biol. Chem.* 263, 7741–7746
42. Carter, W. G., Ryan, M. C., and Gahr, P. J. (1991) *Cell* 65, 599–610
43. Rousselle, P., Lunstrum, G. P., Keene, D. R., and Burgeson, R. E. (1991) *J. Cell Biol.* 114, 567–576
44. König, A., and Bruckner-Tuderman, L. (1991) *J. Invest. Dermatol.* 96, 803–808
45. Murphy, G., Reynolds, J. J., and Werb, Z. (1985) *J. Biol.Chem.* 260, 3079–3083
46. Takahara, K., Brevard, R., Hoffman, G. G., Suzuki, N., and Greenspan, D. S. (1996) *Genomics* 34, 157–165
47. Colige, A., Li, S.-W., Sieron, A. L., Nusgens, B. V., and Prockop, D. J. (1997) *P.N.A.S. U.S.A.* 94, 2374–2379

We claim:

1. A method for evaluating a proposed modulator of procollagen maturation, the method comprising the steps of:
exposing fibrogenic cells to a molecule selected from the group consisting of TGF-β1 and TGF-β2 to induce procollagen-cleavage activity of an endogenous protein selected from the group consisting of bone morphogenetic protein 1, mammalian tolloid, and procollagen N-proteinase;
measuring procollagen-cleavage activity of the endogenous protein secreted from the fibrogenic cells in the presence of the proposed modulator; and
comparing the measured procollagen-cleavage activity against the procollagen-cleavage activity of the protein in the absence of the proposed modulator.

2. The method as claimed in claim 1 wherein the fibrogenic cells are further exposed to ascorbate.

3. The method as claimed in claim 1 wherein the fibrogenic cells are selected from the group consisting of human osteosarcoma cells, murine osteoblastic cells, and human fibroblasts.

4. The method as claimed in claim 1 wherein the fibrogenic cells are selected from the group consisting of MG-63 and MC3T3-E1 cells.

5. A method for evaluating a proposed modulator of procollagen maturation, the method comprising the steps of:
measuring procollagen-cleavage activity of an endogenous secreted protein induced by TGFPβ1 from fibrogenic cells, in the presence of the proposed modulator, the protein being selected from the group consisting of bone morphogenetic protein-1, mammalian tolloid, and procollagen N-proteinase; and comparing the measured procollagen-cleavage activity against the procollagen-cleavage activity of the protein in the absence of the proposed modulator.

6. The method as claimed in claim 5 wherein the fibrogenic cells are further exposed to ascorbate.

7. The method as claimed in claim 5 wherein the fibrogenic cells are selected from the group consisting of human osteosarcoma cells, murine osteoblastic cells, and human fibroblasts.

8. The method as claimed in claim 5 wherein the fibrogenic cells are selected from the group consisting of MG-63 and MC3T3-E1 cells.

* * * * *

UNITED STATES PATENT AND TRADEMARK OFFICE
CERTIFICATE OF CORRECTION

PATENT NO. : 6,037,139
DATED : Mar. 14, 2000
INVENTOR(S) : Daniel S. Greenspan, et al It is certified that error appears in the above-identified patent and that said Letters Patent is hereby corrected as shown below:

Col. 1, line 10, delete "Not Applicable." and insert therefor:

--This invention was made with United States government support awarded by the following agencies:

NIH R01-AR43621; R01-GM46846

The United States Government has certain rights in this invention.--

Signed and Sealed this

Eighth Day of May, 2001

*Attest:*

NICHOLAS P. GODICI

*Attesting Officer*   *Acting Director of the United States Patent and Trademark Office*